US012655462B2

(12) United States Patent
Ridinger et al.

(10) Patent No.: US 12,655,462 B2
(45) Date of Patent: Jun. 16, 2026

(54) PLK1 TARGET PHOSPHORYLATION STATUS AND TREATMENT OF CANCER WITH PLK1 INHIBITORS

(71) Applicant: Cardiff Oncology, Inc., San Diego, CA (US)

(72) Inventors: Maya Ridinger, San Diego, CA (US); Thomas H. Adams, San Diego, CA (US); Mark Erlander, San Diego, CA (US)

(73) Assignee: Cardiff Oncology, Inc., San Diego, CA (US)

( * ) Notice: Subject to any disclaimer, the term of this patent is extended or adjusted under 35 U.S.C. 154(b) by 1188 days.

(21) Appl. No.: 17/271,500

(22) PCT Filed: Aug. 24, 2019

(86) PCT No.: PCT/US2019/048044
§ 371 (c)(1),
(2) Date: Feb. 25, 2021

(87) PCT Pub. No.: WO2020/046767
PCT Pub. Date: Mar. 5, 2020

(65) Prior Publication Data

US 2021/0222228 A1 Jul. 22, 2021

Related U.S. Application Data

(60) Provisional application No. 62/722,934, filed on Aug. 26, 2018.

(51) Int. Cl.

| | |
|---|---|
| ***C12Q 1/48*** | (2006.01) |
| ***A61K 31/517*** | (2006.01) |
| ***C12Q 1/6804*** | (2018.01) |
| ***G01N 33/575*** | (2026.01) |
| ***G01N 33/57555*** | (2026.01) |

(52) U.S. Cl.
CPC ............ *C12Q 1/485* (2013.01); *A61K 31/517* (2013.01); *C12Q 1/6804* (2013.01); *G01N 33/57555* (2026.01); *G01N 33/57585* (2026.01); *C12Y 207/11021* (2013.01); *G01N 2333/912* (2013.01); *G01N 2440/14* (2013.01)

(58) Field of Classification Search
None
See application file for complete search history.

(56) References Cited

U.S. PATENT DOCUMENTS

| | | | | |
|---|---|---|---|---|
| 8,614,220 | B2 | 12/2013 | Caruso et al. | |
| 8,648,078 | B2 | 2/2014 | Zampieri et al. | |
| 8,927,530 | B2 | 1/2015 | Valsasina et al. | |
| 9,765,152 | B2 | 9/2017 | Rojkjaer et al. | |
| 2010/0278779 | A1 | 11/2010 | Zeldis | |
| 2010/0305059 | A1 | 12/2010 | Reddy et al. | |
| 2011/0076693 | A1 | 3/2011 | Lee et al. | |
| 2013/0116225 | A1 | 5/2013 | Sheshbaradaran et al. | |
| 2016/0287592 | A1 | 10/2016 | Chang et al. | |
| 2017/0315127 | A1 | 11/2017 | Gao et al. | |
| 2021/0222228 | A1* | 7/2021 | Ridinger | C12Q 1/6804 |
| 2023/0113501 | A1* | 4/2023 | Ridinger | A61K 31/519 514/157 |
| 2024/0197730 | A1* | 6/2024 | Ridinger | A61K 31/517 |

OTHER PUBLICATIONS

Kumar et al., PLK-1 Targeted Inhibitors and Their Potential against Tumorigenesis, BioMed Research International, vol. 2015, Article ID: 705745, Publication Year: 2015 (Year: 2015).*
Keller et al., Caspase-8 function, and phosphorylation, in cell migration, Seminars in Cell & Developmental Biology 82 (2018) 105-117, Publication Date: Feb. 17, 2018 (Year: 2018).*
Ann Gutteridge et al., Plk1 Inhibitors in Cancer Therapy: From Laboratory to Clinics, Mol. Cancer Ther., 15(7): 1427-1435, Publication Date: Jul. 2016 (Year: 2016).*
Archambault et al., Several inhibitors of the Plk1 Polo-Box Domain turn out to be non-specific protein alkylators, Cell Cycle, vol. 16, No. 12, 1220-1224, Publication Date: Jun. 2, 2017 (Year: 2017).*
Whitley et al., Abstract 2810: Computationally predicted sensitivity of clinicalcohorts identifies drug relationships and biomarkers associated withresponse to PCM-075, a PLK1 selective inhibitor, Cancer Res (2018) 78 (13_Supplement):2810, Publication Date: Jul. 1, 2018 (Year: 2018).*
Sero et al., Targeting polo-like kinase 1 by NMS-P937 in osteosarcoma cell lines inhibits tumor cell growth and partially overcomes drug resistance, Invest New Drugs, (2014) 32: 1167-1180, Publication Date: Sep. 7, 2014 (Year: 2014).*
Weiss et al., Invest New Drugs, 36: 85-95, Publication Date: Jul. 20, 2017 (Year: 2017).*
Acunzo et al., "TCTP as therapeutic target in cancers," Cancer Treatment Reviews 2014, 40(6), 760-769.
Barretina et al., "The Cancer Cell Line Encyclopedia enables predictive modelling of anticancer drug sensitivity," Nature 2012, 483(7391), 603-607.
Basu et al., "An interactive resource to identify cancer genetic and lineage dependencies targeted by small molecules," Cell 2013, 154(5), 1151-1161.
Berg et al., "Polo-like kinases in AML," Expert Opinion on Investigational Drugs 2012, 21(8), 1069-1074.
Beria et al., "NMS-P937, a 4, 5-dihydro-1*H*-pyrazolo [4, 3-*h*] quinazoline derivative as potent and selective Polo-like kinase 1 inhibitor," Bioorganic & Medicinal Chemistry Letters 2011, 21(10), 2969-2974.

(Continued)

*Primary Examiner* — Peter J Reddig
*Assistant Examiner* — Cheng Lu
(74) *Attorney, Agent, or Firm* — Dickinson Wright PLLC

(57) ABSTRACT

Provided is a method comprising determining polo-like kinase 1 (PLK1) activity in a cancer in a patient by measuring phosphorylation of a PLK1 target (a) prior to treatment of (i) the patient or (ii) a cancer sample from the patient with a PLK1 inhibitor, and (b) after the treatment.
Also provided is a method comprising determining polo-like kinase 1 (PLK1) activity in a cancer in a patient by measuring phosphorylation of a PLK1 target without treatment with a PLK1 inhibitor.

9 Claims, 11 Drawing Sheets

(56) References Cited

OTHER PUBLICATIONS

BIORAD, "ELISA—The Essentials," Pocket Guide to ELISA 2023 , in 22 pp.
Casolaro et al., "The Polo-Like Kinase 1 (PLK1) Inhibitor NMS-P937 Is Effective in a New Model of Disseminated Primary $CD56^+$ Acute Monoblastic Leukaemia," Plos One 2013, 8(3), in 11 pages.
Cheson et al., "Revised Recommendations of the International Working Group for Diagnosis, Standardization of Response Criteria, Treatment Outcomes, and Reporting Standards for Therapeutic Trials in Acute Myeloid Leukemia," Journal of Clinical Oncology 2003, 21(24), 4642-4649.
Cucchi et al., "Phosphorylation of TCTP as a Marker for Polo-like Kinase-1 Activity In Vivo," Anticancer Research 2010, 30(12), 4973-4985.
Degenhardt & Lampkin, "Targeting Polo-like Kinase in Cancer Therapy," Clinical Cancer Research 2010, 16(2), 384-389.
Döhner et al., "Randomized, phase 2 trial of low-dose cytarabine with or without volasertib in AML patients not suitable for induction therapy," Blood 2014, 124(9), 1426-1433.
Extended European Search Report dated Apr. 4, 2022 in European Application No. 19855743.1.
Geeleher et al., "Discovering novel pharmacogenomic biomarkers by imputing drug response in cancer patients from large genomics studies," Genome Research 2017, 27(10), 1743-1751.
Gjertsen & Schöffski, "Discovery and development of the Polo-like kinase inhibitor volasertib in cancer therapy," Leukemia 2015, 29(1), 11-19.
Hartsink-Segers et al., "Inhibiting Polo-like kinase 1 causes growth reduction and apoptosis in pediatric acute lymphoblastic leukemia cells," Haematologica 2013, 98(10), 1539-1546.
International Search Report and Written Opinion dated Nov. 14, 2019 in PCT Patent Application No. PCT/US2019/048044.
Liu et al., "PLK1, A Potential Target for Cancer Therapy," Translational Oncology 2017, 10(1), 22-32.
Müller-Tidow et al., "A randomized, open-label, phase I/II trial to investigate the maximum tolerated dose of the P olo-like kinase inhibitor BI 2536 in elderly patients with refractory/relapsed acute myeloid leukaemia," British Journal of Haematology 2013, 163(2), 214-222.
Office Action dated Dec. 23, 2022 in European Application No. 19855743.1.
Office Action dated Mar. 22, 2023 in Chinese Application No. 201980069212.6.
Racila et al., "Detection and characterization of carcinoma cells in the blood," Proceedings of the National Academy of Sciences 1998, 95(8), 4589-4594.
Ridinger et al., "Pharmacodynamic and tumor biomarker analysis of a PLK1 inhibitor, PCM-075, in a phase 1b/2 trial for acute myeloid leukemia," Cancer Research 2018, 78 (13_Supplement), 4833, in 4 pages. https://aacrjournals.org/cancerres/article/78/13_Supplement/4833/629317/Abstract-4833-Pharmacodynamic-and-tumor.
Schöffski et al., "A phase I, dose-escalation study of the novel Polo-like kinase inhibitor volasertib (BI 6727) in patients with advanced solid tumours," European Journal of Cancer 2012, 48(2), 179-186.
Sero et al., "Targeting polo-like kinase 1 by NMS-P937 in osteosarcoma cell lines inhibits tumor cell growth and partially overcomes drug resistance," Investigational New Drugs 2014, 32, 1167-1180.
Trovagene Inc., "Trovagene Receives USAN Approval for "Onvansertib" as Nonproprietary Name. For First-in-Class, 3rd Generation PLK1 Inhibitor Drug Candidate, PCM-075," Trovagene Oncology 2018, in 5 pages.
U.S. National Library of Medicine, "Onvansertib in Combination With Either Low-dose Cytarabine or Decitabine in Adult Patients With Acute Myeloid Leukemia (AML)," ClinicalTrials.gov 2017, in 11 pages. Accessed 2023. https://clinicaltrials.gov/ct2/show/NCT03303339?term=NCT03303339&draw=2&rank=1.
UNIPROT, "P13693—TCTP_HUMAN," uniport.org 2023, in 10 pages.
Valsasina et al., "NMS-P937, an Orally Available, Specific Small-Molecule Polo-like Kinase 1 Inhibitor with Antitumor Activity in Solid and Hematologic MalignanciesNMS-P937, a New Orally Available PLK1-Specific Inhibitor," Molecular Cancer Therapeutics 2012, 11(4), 1006-1016.
Weiss et al., "Phase I dose escalation study of NMS-1286937, an orally available Polo-Like Kinase 1 inhibitor, in patients with advanced or metastatic solid tumors," Investigational New Drugs 2018, 36, 85-95.
Yang et al., "Genomics of Drug Sensitivity in Cancer (GDSC): a resource for therapeutic biomarker discovery in cancer cells," Nucleic Acids Research 2013 , 41(D1), D955-D961.
Zeidan et al., "Preliminary Safety, Pharmacokinetics (PK) and Pharmacodynamic (PD) Analysis of the Polo-like Kinase-1 (PLK1) Inhibitor PCM-075, in Combination with Low-Dose Cytarabine (LDAC) or Decitabine (D) in Patients with Relapsed or Refractory (R/R) Acute Myeloid Leukemia (AML)," Blood 2018, 132, in 3 pages.
Notice of Allowance dated Aug. 5, 2024 in Japanese Application No. 2021-510704.
Office Action dated Aug. 16, 2023 in European Application No. 19855743.1.
Office Action dated Feb. 29, 2024 in Japanese Application No. 2021-510704.
Office Action dated Jan. 10, 2024 in Chinese Application No. 201980069212.6.
Office Action dated Jul. 31, 2023 in Japanese Application No. 2021-510704.
Office Action dated May 14, 2024 in Chinese Application No. 201980069212.6.

* cited by examiner

IMMUNO-PCR FOR DETERMINING PHOSPHORYLATION OF TCTP

PLK1 TARGET PHOSPHORYLATION STATUS AND TREATMENT OF CANCER WITH PLK1 INHIBITORS

CROSS-REFERENCE TO RELATED APPLICATIONS

The present application is a U.S. national phase application under 35 U.S.C. § 371 of International Application No. PCT/US2019/048044, filed on Aug. 24, 2019 and published as WO 2020/046767 A1 on Mar. 5, 2020, which claims priority to U.S. Provisional Application No. 62/722,934, filed on Aug. 26, 2018. The content of each of these related applications is incorporated herein by reference in its entirety.

BACKGROUND OF THE INVENTION

(1) Field of the Invention

The present application generally relates to cancer treatment. More specifically, the application provides methods for evaluating responsiveness of a cancer to a polo-like kinase 1 (PLK1) inhibitor by determining the ability of the PLK1 inhibitor to inhibit phosphorylation of a target of PLK1 in a patient with the cancer.

(2) Description of the Related Art

Polo-Like Kinase 1

Polo-like kinase 1 (PLK1) is the most well characterized member of the 5 members of the family of serine/threonine protein kinases and strongly promotes the progression of cells through mitosis. PLK1 performs several important functions throughout mitotic (M) phase of the cell cycle, including the regulation of centrosome maturation and spindle assembly, the removal of cohesins from chromosome arms, the inactivation of anaphase-promoting complex/cyclosome (APC/C) inhibitors, and the regulation of mitotic exit and cytokinesis (Stebhardt, 2010). It plays a key role in centrosome functions and the assembly of bipolar spindles. It also acts as a negative regulator of p53 family members leading to ubiquitination and subsequent degradation of p53/TP53, inhibition of the p73/TP73 mediated pro-apoptotic functions and phosphorylation/degradation of bora, a cofactor of Aurora kinase A. During the various stages of mitosis PLK1 localizes to the centrosomes, kinetochores and central spindle. PLK1 is aberrantly overexpressed in a variety of human cancers including acute myeloid leukemia (AML), breast, ovarian, non-small cell lung, colon, head and neck, endometrial and esophageal carcinomas and is correlated with cellular proliferation and poor prognosis (Degenhardt, 2010; Liu et al., 2017; Cancer Genome Atlas).

Onvansertib

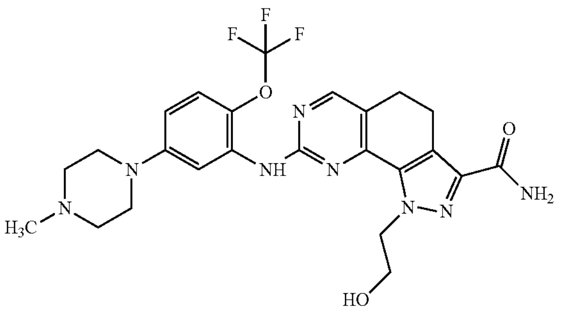

ONVANSERTIB

Onvansertib (also known as PCM-075, NMS-1286937, NMS-937, "compound of formula (I)" in U.S. Pat. No. 8,927,530; IUPAC name 1-(2-hydroxyethyl)-8-{[5-(4-methylpiperazin-1-yl)-2-(trifluoromethoxy)phenyl]amino}-4,5-dihydro-1H-pyrazolo[4,3-h] quinazoline-3-carboxamide) is the first PLK1 specific ATP competitive inhibitor administered by oral route to enter clinical trials with proven antitumor activity in different preclinical models (Beria et al., 2011; Hartsink-Segers et al., 2013; Sero et al., 2014; Valsasina et al., 2012; Casolaro et al., 2013). The compound shows high potency in proliferation assays having low nanomolar activity on a large number of cell lines, both from solid as well as hematologic tumors. Onvansertib potently causes a mitotic cell-cycle arrest followed by apoptosis in cancer cell lines and inhibits xenograft tumor growth with a clear PLK1-related mechanism of action at well tolerated doses in mice after oral administration. In addition, onvansertib shows activity in combination therapy with approved cytotoxic drugs, such as irinotecan, in which there is enhanced tumor regression in HT29 human colon adenocarcinoma xenografts compared to each agent alone (Valsasina et al., 2012; see also U.S. Pat. No. 8,927,530), and shows prolonged survival of animals in a disseminated model of AML in combination therapy with cytarabine (Valsasina et al., 2012; Casolaro et al., 2013). Onvansertib has favorable pharmacologic parameters and good oral bioavailability in rodent and nonrodent species, as well as proven antitumor activity in different nonclinical models using a variety of dosing regimens, which may potentially provide a high degree of flexibility in dosing schedules, warranting investigation in clinical settings. Onvansertib has several advantages over previous PLK inhibitors, including high selectivity for PLK1 only, oral availability and half-life of ~24 hours.

A Phase 1 dose-escalation study with onvansertib has been conducted in adult subjects with advanced/metastatic solid tumors at a single study site in the US. The primary objective of that study was to determine a maximum tolerated dose (MTD) of onvansertib in adult subjects with advanced/metastatic solid tumors. Secondary objectives of the study were to define antitumor activity. In that study, a recommended phase 2 dose of 24 $mg/m^2$ was established and 5 of 16 evaluable patients had stable disease.

Based on the above, there is a need for a method that enriches for the subset of subjects that have a greater likelihood of responding to onvansertib or other PLK1 inhibitors. The present invention satisfies that need by providing methods that predict the efficacy of a PLK1 inhibitor on a cancer by determining the extent of inhibition of phosphorylation of a PLK1 target by the PLK1 inhibitor.

BRIEF SUMMARY OF THE INVENTION

Provided is a method comprising determining polo-like kinase 1 (PLK1) activity in a cancer in a patient by measuring phosphorylation of a PLK1 target (a) prior to treatment of (i) the patient or (ii) a cancer sample from the patient with a PLK1 inhibitor, and (b) after the treatment.

DETAILED DESCRIPTION OF THE INVENTION

Figure 1A:
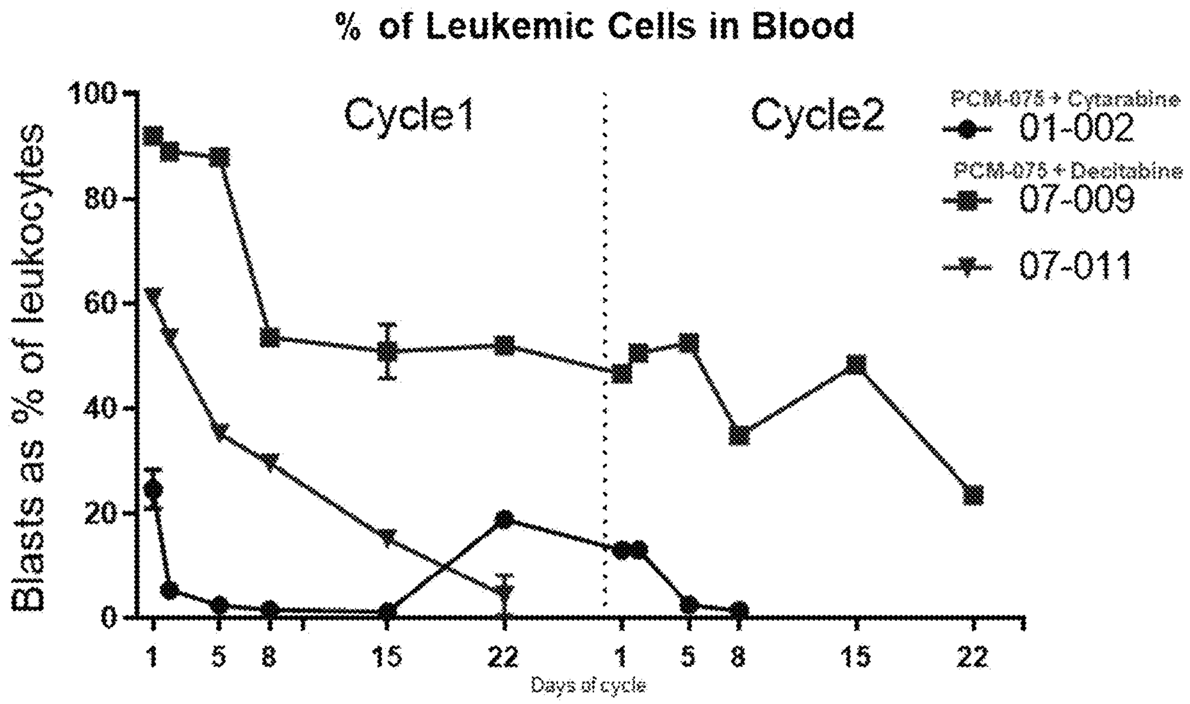
FIG. 1A is a graph showing leukemic cells in blood of three patients treated with onvansertib (PCM-075) and either cytarabine or decitabine.

As used herein, the singular forms “a”, “an” and “the” are intended to include the plural forms as well, unless the context clearly indicates otherwise. Additionally, the use of “or” is intended to include “and/or”, unless the context clearly indicates otherwise.

The present invention is based in part on the discovery that the effectiveness of a PLK1 inhibitor in treating a cancer in a patient can be quickly and easily determined by determining whether the PLK1 inhibitor is able to inhibit PLK1 activity in cells of the cancer. That discovery is established by the studies described in Examples below. Those Examples establish that inhibition of phosphorylation of a PLK1 target (TCTP) from a cancer (acute myeloid leukemia) in a patient by a PLK1 inhibitor (onvansertib) identifies a cancer that responds to treatment of the patient with the PLK1 inhibitor. With those results, the skilled artisan would understand that a measurement of inhibition of phosphorylation of any PLK1 target in any cancer in any patient by any PLK1 inhibitor would identify a cancer that responds to treatment with that PLK1 inhibitor.

Thus, in some embodiments, the present invention is directed to a method comprising determining polo-like kinase 1 (PLK1) activity in a cancer in a patient by measuring phosphorylation of a PLK1 target (a) prior to treatment of (i) the patient or (ii) a cancer sample from the patient with a PLK1 inhibitor, and (b) after the treatment.

In these methods, phosphorylation of any PLK1 target can be measured. Nonlimiting examples of PLK1 phosphorylation targets that can be evaluated for reduced phosphorylation include TRF1, Mre11, PTP1B, Orc2, Hbo1, BubR1, WDR62, IRS2, LSD1, caspase-8, NudC, PTEN, BORA, BUB1B/BUBR1, CCNB1, CDC25C, CEP55, ECT2, ERCC6L, FBXO5/EMI1, FOXM1, KIF20A/MKLP2, CENPU, NEDD1, NINL, NPM1, NUDC, PKMYT1/MYT1, KIZ, PPP1R12A/MYPT1, PRC1, RACGAP1/CYK4, SGO1, STAG2/SA2, TEX14, TOPORS, p73/TP73, WEE1, HNRNPU and translational control tumor protein (TCTP). In some embodiments, the PLK1 target that is evaluated for phosphorylation inhibition is TCTP (UniProtKB P13693). PLK1 phosphorylates TCTP at serine 46 and threonine 65 (Cucchi et al, 2010; Acunzo et al., 2014).

In some embodiments, the patient is treated with the PLK1 inhibitor and a sample of the cancer is taken before and after that treatment, and phosphorylation of the target is measured in those samples, to determine whether the PLK1 inhibitor is effective. In other embodiments, cancer cells (e.g., in blood, lymph, bone marrow or tissue such as biopsy tissue or cells from a needle aspiration) are removed from the patient’s body, and those cells are treated with the PLK1 inhibitor in vitro. Such samples can be any tissue or bodily fluid where the cancer is present.

The cancer cells that are evaluated in these methods can be in tissue or in a liquid of the patient, e.g., any liquid or tissue harboring any of the cancers identified below, for example, the blood, a tissue aspirate, bone marrow, urine etc. of the patient. In some embodiments where the cancer is in the blood of the patient, the cells to be utilized to evaluate PLK1 inhibition can be taken in a sample of the patient’s lymph, bone marrow or blood. Any cancer in the blood of a patient can be evaluated by these methods. In some embodiments, the cancer is acute myeloid leukemia (AML), B-cell lymphoma, or from a metastatic tumor. Methods to evaluate cells from metastatic tumors in blood are known in the art. See, e.g., Racila et al., 1998.

These methods are not narrowly limited to any particular time after treatment with the PLK1 inhibitor that the sample is taken and evaluated for inhibition of phosphorylation of the PLK1 target. The determination of the time interval after treatment that the sample is taken for any PLK1 target and PLK1 inhibitor treatment can be made without undue experimentation. Where the PLK1 inhibitor is onvansertib (oral administration, half-life about 24 hours) and the PLK1 target is TCTP, it is believed that the sample can be taken and evaluated anytime from 1 to 24 hours after treatment. In some embodiments, the phosphorylation of the PLK1 target is determined at least two hours after treatment. In other embodiments, the phosphorylation of the PLK1 target is determined at least about three hours after treatment.

This method can be utilized in cells of any cancer. Exemplary cancers include, but are not limited to, acute lymphoblastic leukemia, AML, adrenocortical carcinoma, adrenocortical carcinoma, AIDS-related cancers, AIDS-related lymphoma, anal cancer, appendix cancer, childhood cerebellar astrocytoma, childhood cerebral astrocytoma, basal cell carcinoma, skin cancer (non-melanoma), extrahepatic bile duct cancer, bladder cancer, bone cancer, osteosarcoma and malignant fibrous histiocytoma, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, mycosis fungoides, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, islet cell tumors (endocrine pancreas), Kaposi Sarcoma, kidney (renal cell) cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, non-small cell lung cancer, small cell lung cancer, AIDS-related lymphoma, non-Hodgkin lymphoma, primary central nervous system lymphoma, Waldenstrom macroglobulinemia, medulloblastoma, melanoma, intraocular (eye) melanoma, Merkel cell carcinoma, mesothelioma malignant, mesothelioma, metastatic squamous neck cancer, mouth cancer, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, soft tissue sarcoma, uterine sarcoma, skin cancer (nonmelanoma), skin cancer (melanoma), Merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter, gestational trophoblastic tumor, urethral cancer, endometrial uterine cancer, uterine sarcoma, vaginal cancer, vulvar cancer, and Wilms Tumor.

In some embodiments, the cancer has elevated PLK1 activity when compared to non-cancerous cells. Nonlimiting examples of such cancers include ovarian cancer, breast cancer, colon cancer, lung cancer, pancreatic cancer, prostate cancer, skin cancer, squamous cell carcinoma, a hematopoietic tumor of lymphoid lineage, a hematopoietic tumor of myeloid lineage, a tumor of the central or peripheral nervous system, acute myeloid leukemia, B-cell lymphoma, adrenocortical, esophageal, stomach, and head and neck cancer.

In specific embodiments, the cancer is AML. In various embodiments, the patient has myelodysplastic syndrome.

In some embodiments, after the first determination prior to treatment with the PLK inhibitor, the determined PLK1 activity is compared with normal, i.e., non-cancerous, PLK1 activity, and the patient or cancer sample is not treated with the PLK1 inhibitor unless PLK1 activity is elevated in the cancer. The rationale for these embodiments, is that PLK1 inhibitor treatment is most likely to benefit patients with cancers that have elevated PLK1 activity. In some embodiments, the patient or cancer sample is not treated with the PLK1 inhibitor if PLK1 activity is below normal.

As used herein, "normal" PLK1 activity is PLK1 activity in non-cancerous cells, either from the patient or average in a population, preferably in tissues or cells that are matched or similar to the cancerous tissue.

Any PLK1 inhibitor can be evaluated using these methods. Nonlimiting examples include onvansertib, BI2536, volasertib (BI 6727), GSK461364, HMN-176, HMN-214, AZD1775, CYC140, rigosertib (ON-01910), MLN0905, TKM-080301, TAK-960 or Ro3280. In some embodiments, the PLK1 inhibitor is onvansertib. In some of those embodiments, the cancer is AML.

The phosphorylation of the PLK1 target (e.g., TCTP) can be determined by any method known in the art. In some embodiments, the phosphorylation is determined immunochemically, e.g., using antibodies that (a) bind to the unphosphorylated target and (b) bind to the phosphorylated, but not the unphosphorylated target. These methods are not narrowly limited to any particular immunochemical method. Examples of methods that can be utilized include western blot (as in Example 1 below), dot blot, ELISA, immunohistochemistry, and immuno-PCR (for pTCTP detection).

Immuno-PCR is analogous to ELISA, except that an oligonucleotide is the signal-generating moiety rather than an enzyme. The signal from the oligonucleotide is generated by polymerase chain reaction (PCR) amplification. Because PCR amplifies the oligonucleotide many fold, normally resulting in a dye-labeled amplification product, immuno-PCR is extremely sensitive, and, when used in the present methods, is able to detect a very small amount of phosphorylated TCTP.

Since immuno-PCR is analogous to ELISA, immuno-PCR can be utilized in any format for detecting pTCTP that has been described to detect other proteins with ELISA, for example direct, indirect, sandwich or competitive formats, using any solid phase (e.g., microtiter plates, beads, etc.) known in the art (see, e.g., BioRad, 2017).

Figure 10:
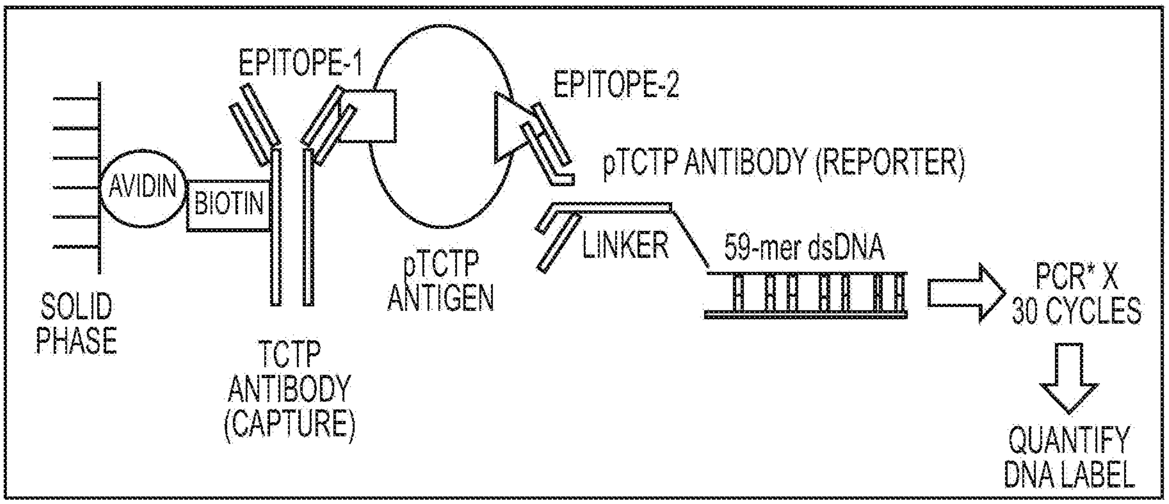
FIG. 10 is an illustration of an example of immuno-PCR for determining phosphorylation of TCTP.

A diagram of a non-limiting example of immuno-PCR for detecting pTCTP is provided in FIG. 10. In that example, avidin is covalently or noncovalently bound to a solid phase. A biotin-labeled TCTP capture antibody, which binds to a first epitope ("EPITOPE-1") on phosphorylated TCTP ("pTCTP") is bound to the avidin. A sample suspected of having pTCTP is added, then a TCTP reporter antibody is then added. In this assay, either the capture antibody or the reporter antibody can bind to pTCTP but not to unphosphorylated TCTP. In some embodiments, the reporter antibody can bind to pTCTP but not to unphosphorylated TCTP. A double stranded DNA molecule (dsDNA) is on the reporter antibody. PCR to amplify the dsDNA is then conducted. There will be a PCR product only if the sample had pTCTP; the amount of that PCR product is proportional to the amount of pTCTP in the sample. The PCR product can then be quantified to determine the amount of pTCTP that is present in the sample.

In any of the above methods, phosphorylation of any amino acid residue of the target protein can be measured. For example, with the target TCTP, phosphorylation of serine 46 or threonine 65, or both, can be measured.

These methods can be utilized to determine the effectiveness of the PLK1 inhibitor on the cancer. This is demonstrated in Example 1 below, where the PLK1 inhibitor onvansertib inhibited phosphorylation in the PLK1 target TCTP in AML cells in patients that responded to onvansertib but not in AML cells in patients that did not respond to onvansertib.

The present invention also encompasses certain variations of the above methods. For example, rather than evaluating PLK1 inhibition in cells of the cancer, cell-free PLK1 and/or the PLK1 target (e.g., TCTP) in patient serum can be evaluated for inhibition of target phosphorylation when exposed to the PLK1 inhibitor. For this variation, a very sensitive method, for example immuno-PCR, may be utilized to determine inhibition of phosphorylation.

In an additional variation, the ability of a PLK1 inhibitor to inhibit PLK1 in a cancer can be determined by determining the ability of the PLK1 inhibitor to inhibit PLK1 activity in the cancer using the methods described herein.

As demonstrated in the Examples below, the inhibition of phosphorylation of a PLK1 target by a PLK1 inhibitor indicates that the PLK1 inhibitor is effective against the cancer. These methods can therefore be used to make an early determination of whether the PLK1 inhibitor is effective.

The determination of the percentage of inhibition of PLK1 target phosphorylation that indicates effectiveness of a particular PLK1 inhibitor can be made without undue experimentation and depends on the PLK1 target, the PLK1 inhibitor, the time after treatment that a sample is taken for testing, how effectiveness of treatment is measured, and on the relative number of false positives or false negatives that are desired. For example, in the Examples below, when the percent inhibition was set at 50%, there was one false negative (starred bar in FIG. 9B), where the inhibition of pTCTP was only 40%, but the PLK1 inhibitor treatment caused a large reduction in % bone marrow blast and an objective response in that patient. With a percentage inhibition set at 35%, there would be no false negatives. The percent inhibition that indicates effectiveness of PLK1 inhibitor treatment can thus be set at any percentage, e.g., 30%, 35%, 40%, 45%, 50%, 55% or 60%, or any other percentage.

Thus, in some embodiments, a reduction of at least 30%, 35%, 40%, 45%, 50%, 55% or 60% in the phosphorylation of the PLK1 target after treatment indicates that the treatment is effective.

The above methods can be utilized to identify candidates in a trial of the efficacy of the PLK1 inhibitor against the cancer. In some embodiments of that application, the patient is not eligible for participation in the trial if the phosphorylation of the PLK1 target is not reduced at least 30%, 35%, 40%, 45%, 50%, 55% or 60% after the treatment relative to the phosphorylation of TCTP before the treatment.

The determination of the effectiveness of the PLK1 inhibitor treatment described above can be utilized to decide whether to therapeutically treat the patient with the PLK1 inhibitor, where the patient is only treated with the PLK1 inhibitor if the percentage of reduction of phosphorylation of the PLK1 target is above the threshold set as described above. Thus, in some embodiments, the patient is therapeutically treated with the PLK1 inhibitor only if the phosphorylation of TCTP is reduced at least 30%, 35%, 40%, 45%, 50%, 55% or 60% after the treatment relative to the phosphorylation of TCTP before the treatment.

These methods can be used when the PLK1 inhibitor is used alone in treating the cancer, or when the patient is also being treated, or being considered for treatment, of the cancer with a PLK1 inhibitor in combination with one or more anti-neoplastic agent that is not a PLK1 inhibitor. Non-limiting examples of such anti-cancer agents are cisplatin, cytarabine, decitabine, doxorubicin, gemcitabine, paclitaxel, SN38, sorafenib, velcade, abiraterone, ibrutinib, acalabrutinib, azacitidine, venetoclax, CPT11, 5FU, bevacizumab, bortezomib, a histone deacetylase inhibitor. In various embodiments, the patient continues treatment with the anti-cancer agent whether or not the patient is therapeutically treated with the PLK1 inhibitor.

In some embodiments, the cancer is acute myeloid leukemia (AML) and the patient is also being treated, or being considered for treatment (alone or in combination with a PLK1 inhibitor), with cytarabine, azacitidine, venetoclax, decitabine, a FLT3 inhibitor, or a combination thereof.

In other embodiments, the cancer is non-Hodgkin lymphoma and the patient is also being treated, or being considered for treatment, with a histone deacetylase inhibitor, ibrutinib, acalabrutinib, venetoclax, or a combination thereof.

In additional embodiments, the cancer is castration resistant or castration sensitive prostate cancer and the patient is also being treated, or being considered for treatment, with abiraterone, an anti-androgen, or a combination thereof.

In further embodiments, the cancer is an adenocarcinoma, e.g., pancreatic, breast or colon adenocarcinoma, and the patient is also being treated, or being considered for treatment, with paclitaxel, sorafenib, bortezomib, cisplatin, SN38, CPT11, 5FU, bevacizumab, gemcitabine, or a combination thereof.

In other embodiments, the cancer is promyelocytic leukemia and the patient is also being treated, or being considered for treatment, with paclitaxel, doxorubicin, cytarabine, or a combination thereof.

In additional embodiments, the cancer is multiple myeloma and the patient is also being treated, or being considered for treatment, with carfilzomib, ixazomib, bortezomib, thalidomide, lenalidomide, pomaidomide, a corticosteroid, or a combination thereof.

In further embodiments, the patient has myelodysplastic syndrome (MDS) and the patient is also being treated, or being considered for treatment, with cytarabine, azacitidine, venetoclax, decitabine, a FLT3 inhibitor, or a combination thereof.

Also provided herewith is a method comprising determining polo-like kinase 1 (PLK1) activity in a cancer in a patient by measuring phosphorylation of a PLK1 target without treatment with a PLK1 inhibitor. In some embodiments, the PLK1 activity is compared to normal activity.

These methods allow for the evaluation of the level of PLK1 activity in the cancer before any PLK1 inhibitor treatment. In some embodiments, if the PLK1 activity in the cancer is elevated, the patient is treated with a PLK1 inhibitor, and if the PLK1 activity in the cancer is not elevated, the patient is not treated with a PLK1 inhibitor. In other embodiments, if the PLK1 activity in the cancer is elevated or normal, the patient is treated with a PLK1 inhibitor, and if the PLK1 activity in the cancer is below normal, the patient is not treated with a PLK1 inhibitor.

In various embodiments of these methods, if the patient or sample is treated with a PLK1 inhibitor, PLK1 activity in the cancer is then determined by any of the methods described herein.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Inhibition of Phosphorylation of Translational Control Tumor Protein (TCTP) by Onvansertib Predicts Response to Polo-Like Kinase 1 (PLK1) Inhibitor Treatment of Acute Myeloid Leukemia

Introduction

This study is directed to the determination of whether the inhibition of phosphorylation of TCTP in cells of AML in patient blood by an inhibitor of PLK1, onvansertib, is predictive of the efficacy of onvansertib treatment for AML. The data establishes that onvansertib inhibition of TCTP phosphorylation in AML cells does predict response of AML to onvansertib treatment.

Materials and Methods

Patient data provided herein is from patients in clinical trial NCT03303339, Onvansertib in Combination With Either Low-dose Cytarabine (LDAC) or Decitabine in Adult Patients With Acute Myeloid Leukemia (AML) (ClinicalTrials.gov).

Determination of phosphorylation of serine 46 of TCTP in blood was as follows. Peripheral blood mononuclear cells (PBMC) were isolated from a Cellsave blood tube (Menarini Silicon Biosystems) using Leucosep centrifuge tubes (VWR) and Histopaque-1077 (Sigma) according to the manufacturer's recommendations.

Protein extracts were prepared from PBMC and cell lines using M-PER buffer (ThermoFisher) with 150 mM NaCl and 1× protease and phosphatase inhibitors cocktails (ThermoFisher). Protein concentration was measured with the Pierce BCA protein assay kit (ThermoFisher).

Western blots were performed as Simple Western™ assays using the Wes system (ProteinSimple), a combination of capillary electrophoresis and immunodetection techniques, following the manufacturer's protocols. Briefly, extracts with equal protein concentration were mixed with 0.1× sample buffer and 5× fluorescent master mix. Denatured protein samples, biotinylated ladder (ProteinSimple), primary antibodies, horseradish peroxidase (HRP)-conjugated secondary antibody (ProteinSimple), chemiluminescence substrate and wash buffer were dispensed into respective wells of the assay plate and placed in Wes equipment. Primary antibodies were purchased from Cell Signaling Technology: phospho-TCTP-Ser46 (#5251) and TCTP (#5128), and used at a concentration of 1:50. Quantitative analysis was performed using Compass software (ProteinSimple). Signal intensity (area) of pTCTP was normalized to the peak area of TCTP and reported as % pTCTP.

PLK1 inhibition in patients was assessed in blood taken 3-hours following administration of onvansertib at peak concentration ($C_{max}$).

Responders were defined as patients showing a decrease in circulating and bone marrow blasts during treatment.

Results

Figure 1B:
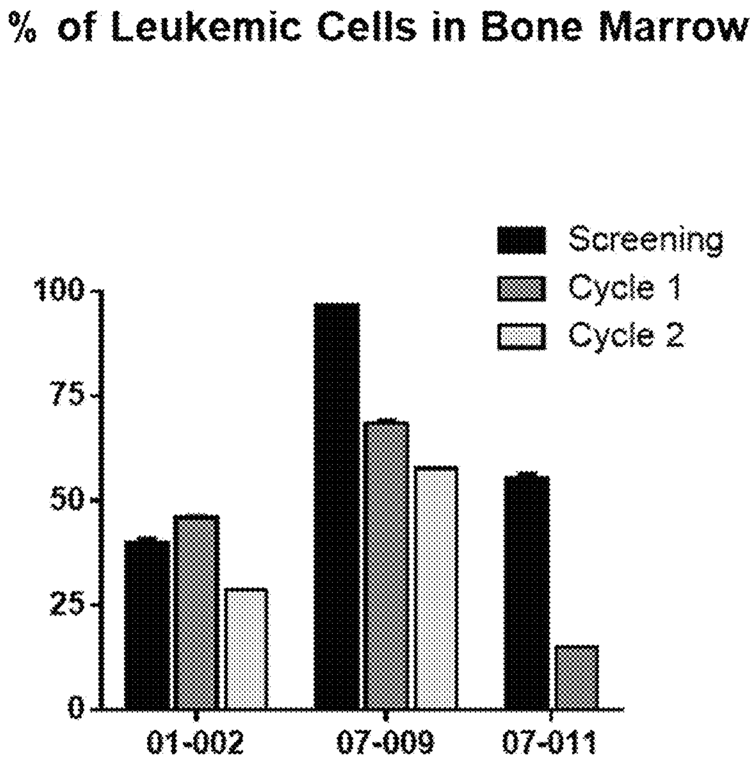
FIG. 1B is a graph showing leukemic cells in bone marrow of three patients treated with onvansertib.

Three of 6 patients treated with onvansertib in combination with low-dose cytarabine (LDAC) or decitabine exhibited a response to the treatment, as shown by decreases in the percentage of leukemic cells in blood (FIG. 1A) and bone marrow (FIG. 1B), with 2 patients (07-009 and 07-011) having decreases in bone marrow from 96% to 55% and 55% to 15%, respectively.

Figure 2A:
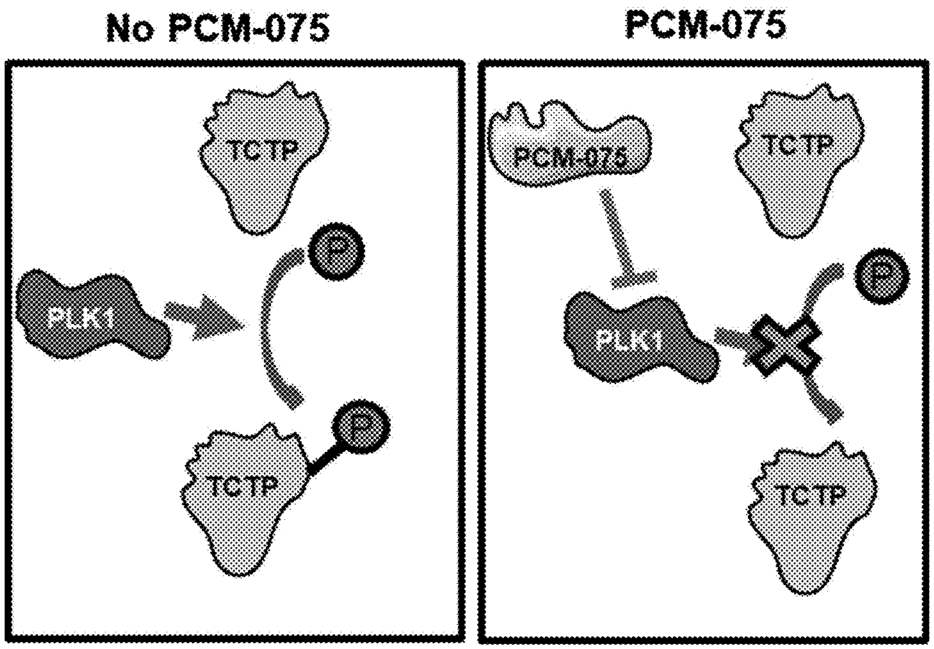
FIG. 2A is illustrations of PLK1 phosphorylation of TCTP inhibited by onvansertib (PCM-075).
Figure 2B:
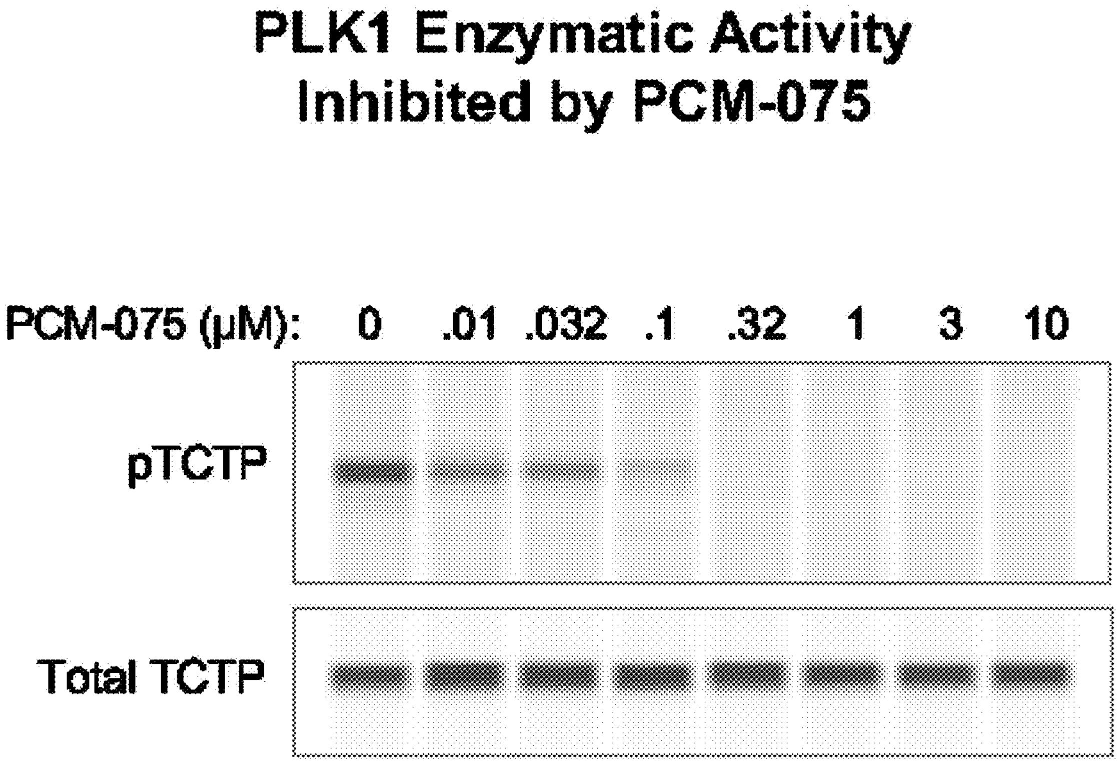
FIG. 2B shows western blots of PLK1 phosphorylation of TCTP inhibited by onvansertib (PCM-075).

If effective in inhibiting PLK1 in vivo, onvansertib should prevent TCTP phosphorylation, as illustrated in FIG. 2A, particularly since onvansertib inhibits pTCTP in vitro, in a dose-dependent manner (FIG. 2B).

Figure 2C:
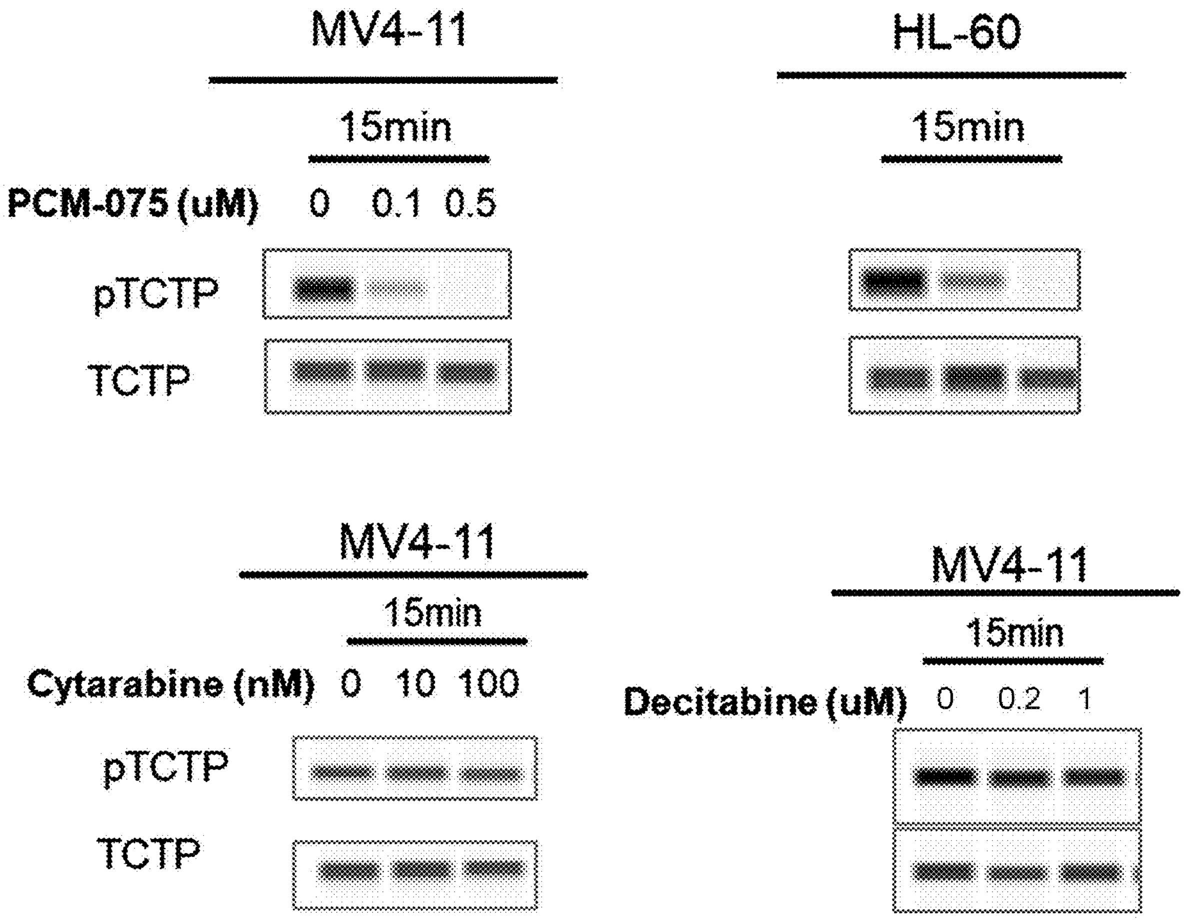
FIG. 2C shows western blots of tests of onvansertib (PCM-075) inhibition of PLK1 phosphorylation of TCTP in AML cell lines.

AML cell lines MV4-11 and HL-60 were treated for 15 minutes with onvansertib (PCM-075) (0.1 or 0.5 μM), cytarabine (10 or 100 nM) or decitabine (0.2 or 1 μM). Proteins were then extracted from the cells and assessed for pTCTP. As shown in FIG. 2C, onvansertib, but not cytarabine or decitabine, inhibited pTCTP.

Figure 3A:
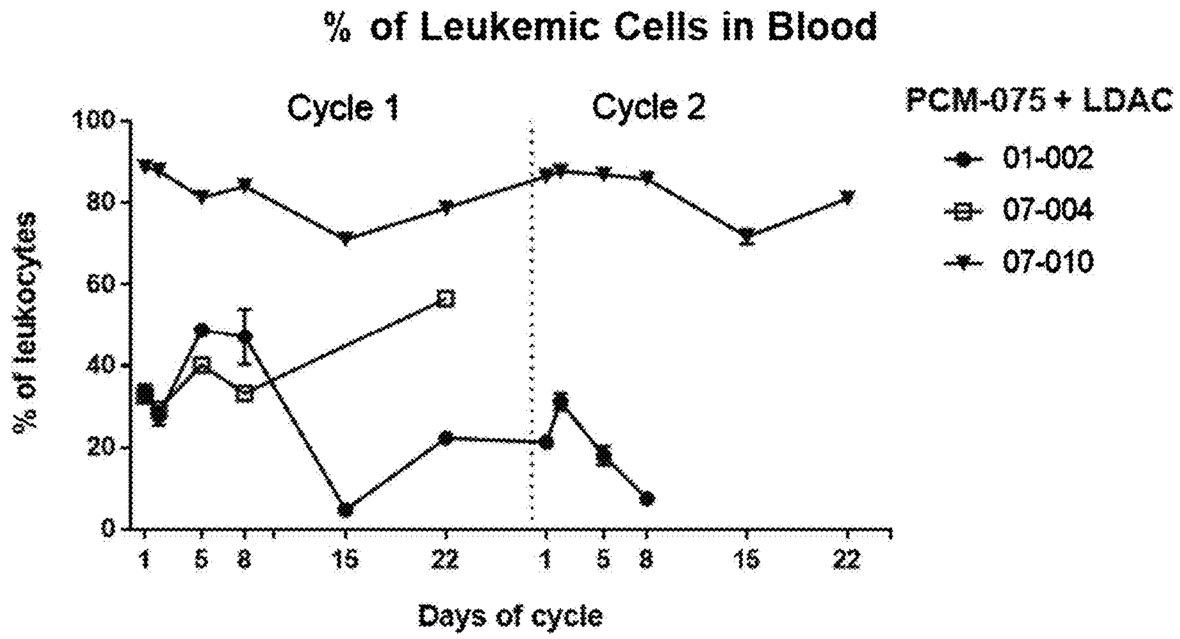
FIG. 3A is a graph showing leukemic cells in blood of three patients treated with onvansertib (PCM-075) and LDAC (cytarabine).
Figure 3B:
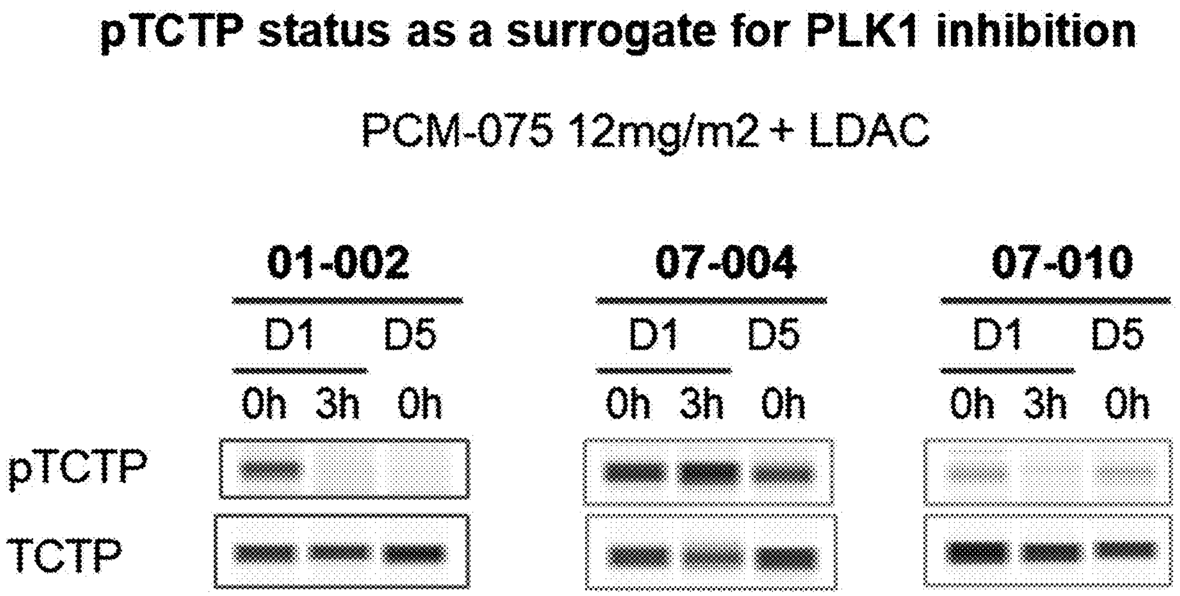
FIG. 3B shows western blots of PLK1 phosphorylation of TCTP before and after onvansertib (PCM-075) treatment of the patients identified in FIG. 3A.

FIG. 3A shows percentage of leukemic cells in blood in three patients that were administered onvansertib and LDAC (cytarabine). Patient 01-002 responded to the treatment, and the other two patients did not. As shown in FIG. 3B, only the responder showed a decrease in pTCTP, as early as three hours from the initiation of treatment.

Figure 4A:
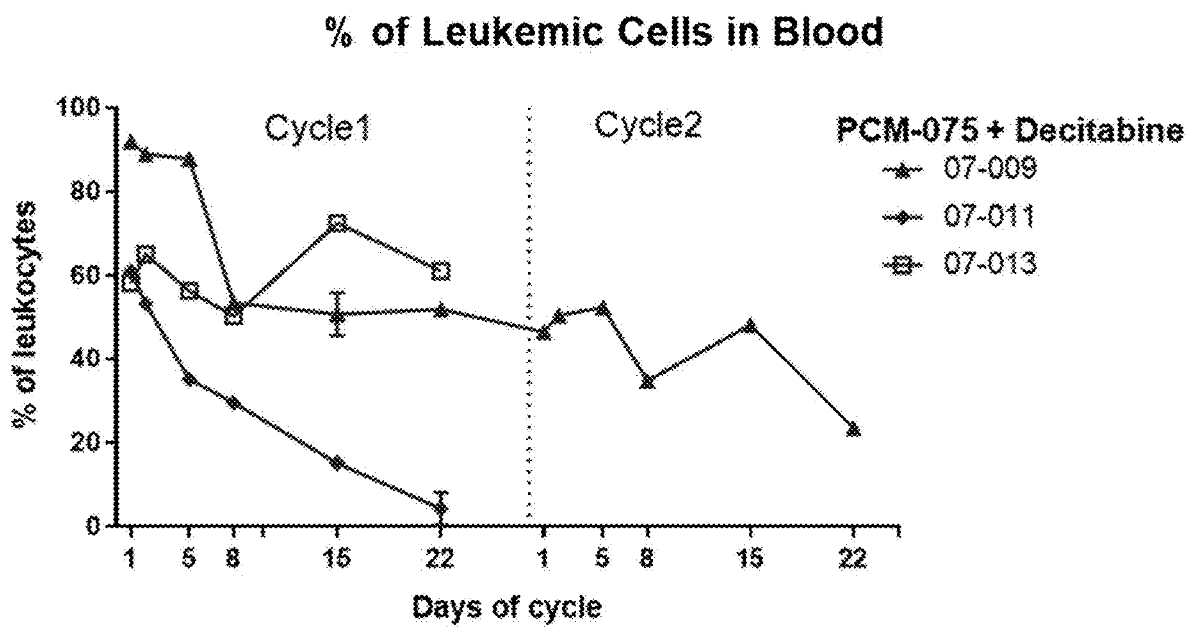
FIG. 4A is a graph showing leukemic cells in blood of three patients treated with onvansertib (PCM-075) and decitabine.

FIG. 4A shows percentage of leukemic cells in blood in three patients that were administered onvansertib and decitabine. Patients 07-009 and 07-011 both responded to the treatment, and patient 07-013 did not. As shown in FIG. 3B, only the two responders showed a decrease in pTCTP, both as early as three hours.

Figure 4B:
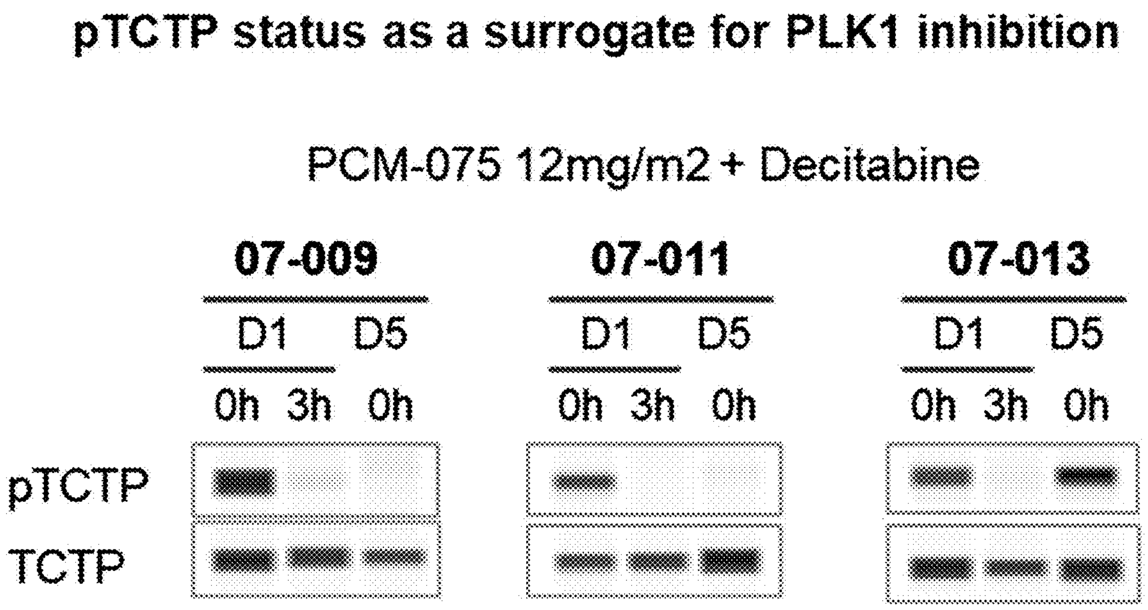
FIG. 4B shows western blots of PLK1 phosphorylation of TCTP before and after onvansertib (PCM-075) treatment of the patients identified in FIG. 4A.

The data in FIGS. 3 and 4 show that responders can be identified within 5 days of starting treatment using the TCTP phosphorylation method described herein, while responders could not be identified until 15 days or longer by determining % leukemic cells in blood.

Figure 5:
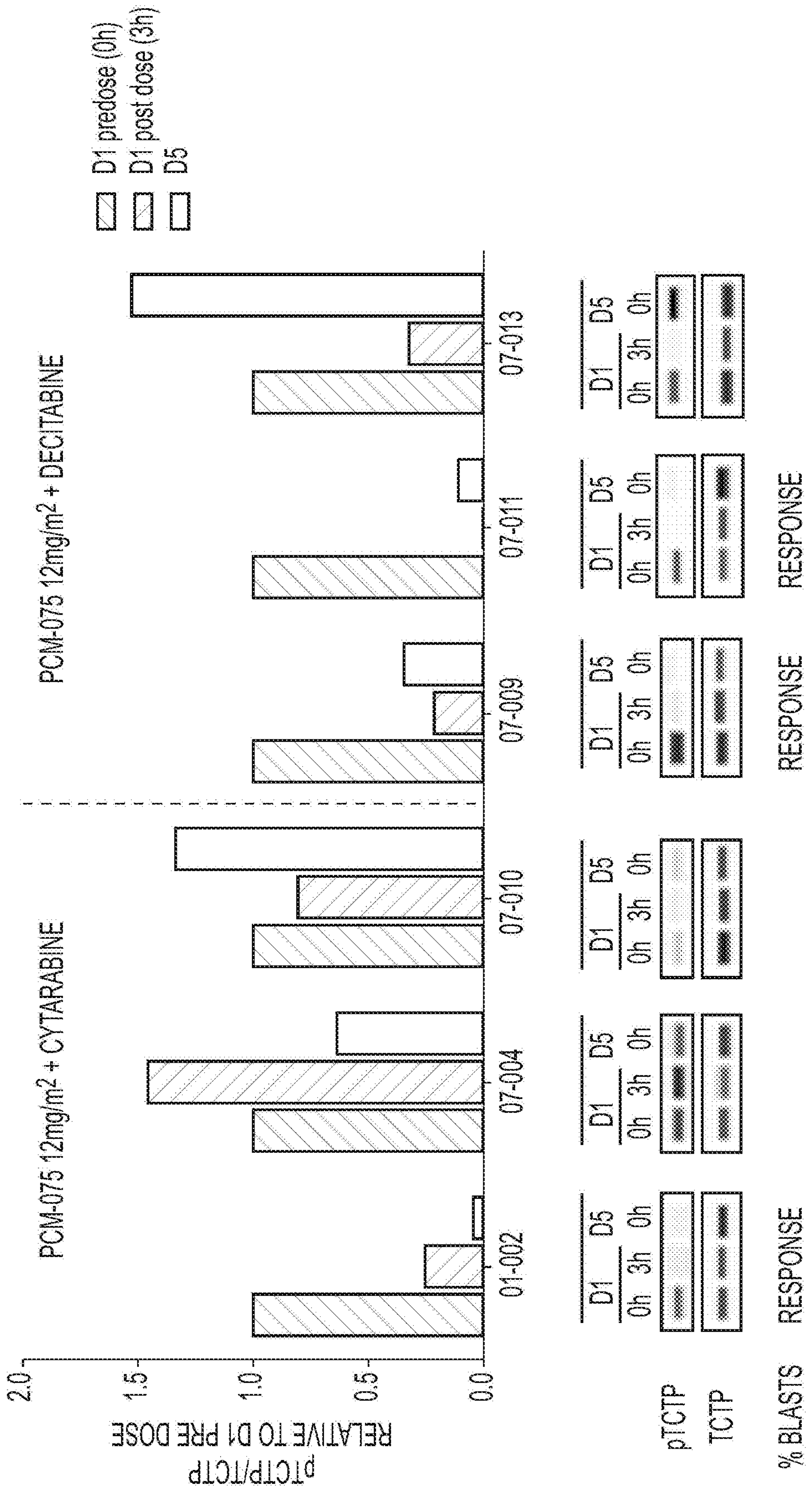
FIG. 5 shows western blots and graphs quantifying the western blots of PLK1 phosphorylation of TCTP before and after onvansertib (PCM-075) treatment of the patients identified in FIGS. 3 and 4.

FIG. 5 shows the quantification of the western blots of FIGS. 3 and 4. The responders could be easily identified in the western blots.

Figure 6:
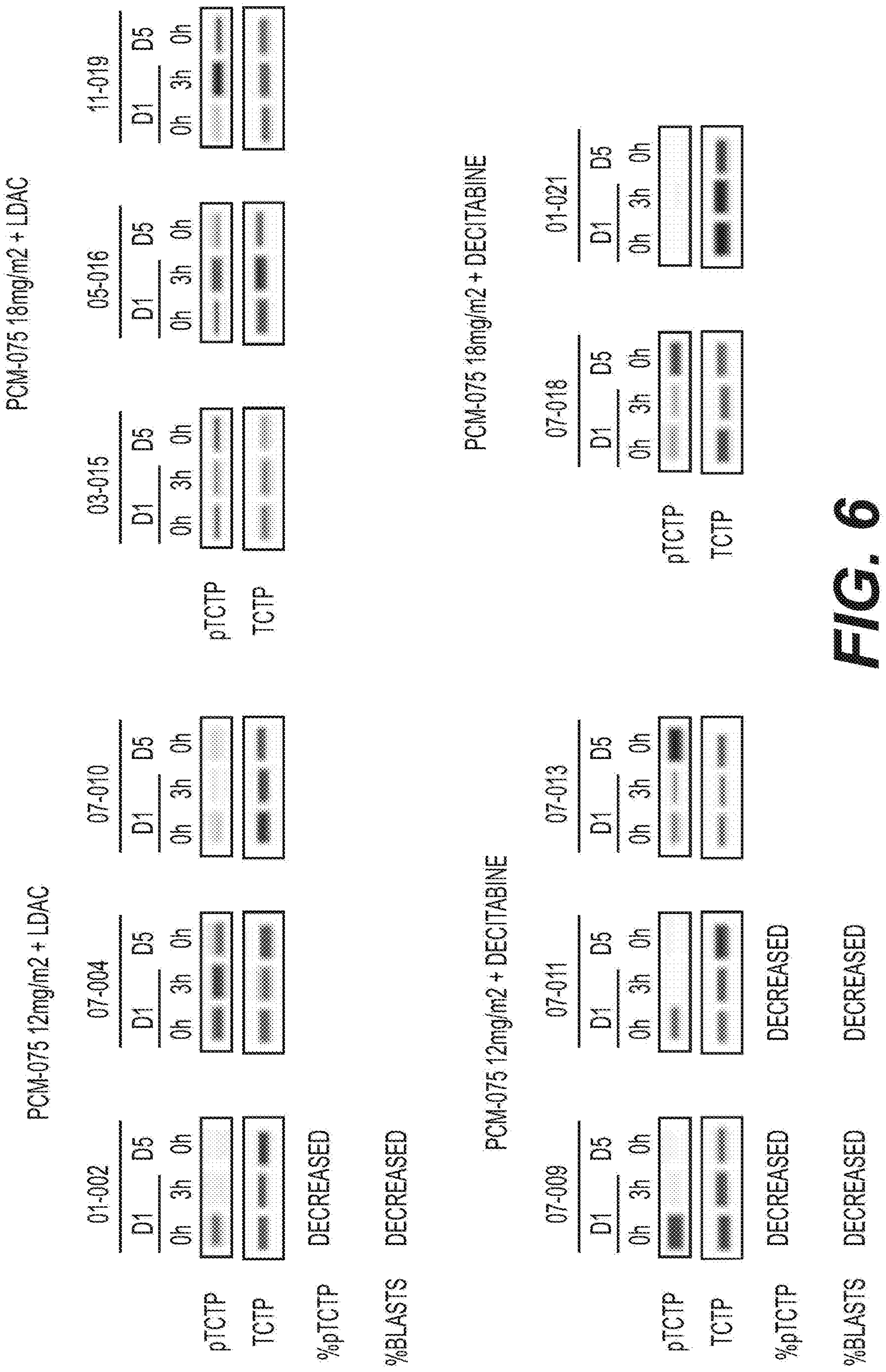
FIG. 6 shows western blots of PLK1 phosphorylation of TCTP before and after treatment of patients with one dose (D1) or four doses (D5) of onvansertib (PCM-075).

To determine whether a higher dose of onvansertib could reduce pTCTP in non-responders, blood cells of patients that were administered 18 mg/$m^2$ were analyzed. FIG. 6 shows western blots of the six patients described in FIGS. 3 and 4, treated at 12 mg/$m^2$ along with western blots of 5 non-responders that were treated at the higher dose. Even at a higher dose of onvansertib, the cells of non-responders did not show a decrease of pTCTP in response to treatment.

Figure 7:
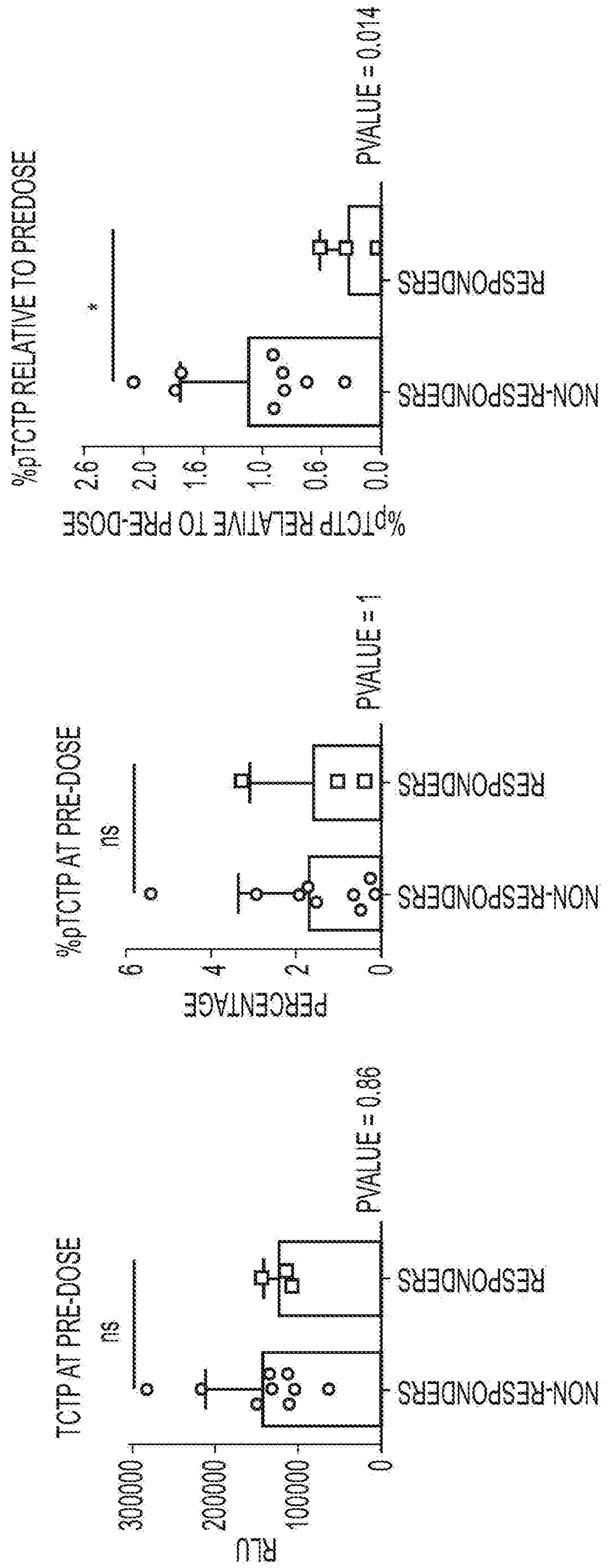
FIG. 7 is graphs of data of % pTCTP before and after treatment of responders and non-responders with onvansertib.

Levels of pTCTP in responders and non-responders were analyzed for differences pre- and post-treatment with onvansertib. As shown in FIG. 7, there were no differences in pTCTP levels prior to treatment. Decrease in pTCTP at post-treatment was significantly higher in responders versus non-responders.

Example 2. Inhibition of Phosphorylation of TCTP by Onvansertib Predicts Response to Polo-Like Kinase 1 (PLK1) Inhibitor Treatment of Acute Myeloid Leukemia The methods described in Example 1 were used to determine the ability of onvansertib treatment, at increased dose, to inhibit phosphorylation of TCTP and the ability to use that inhibition to predict disease responsiveness to that treatment.

Blood samples were collected before, and 3 hours after, onvansertib treatment from patients enrolled in the trial described in Example 1. The onvansertib treatments were 12, 18, 27, or 40 $mg/m^2$. pTCTP and TCTP were assessed by Western-Blot and % pTCTP (pTCTP/TCTP) was quantified.

In these studies, biomarker positivity was defined as ≥50% decrease in % pTCTP from T=0 to T=3h.

Figure 8:
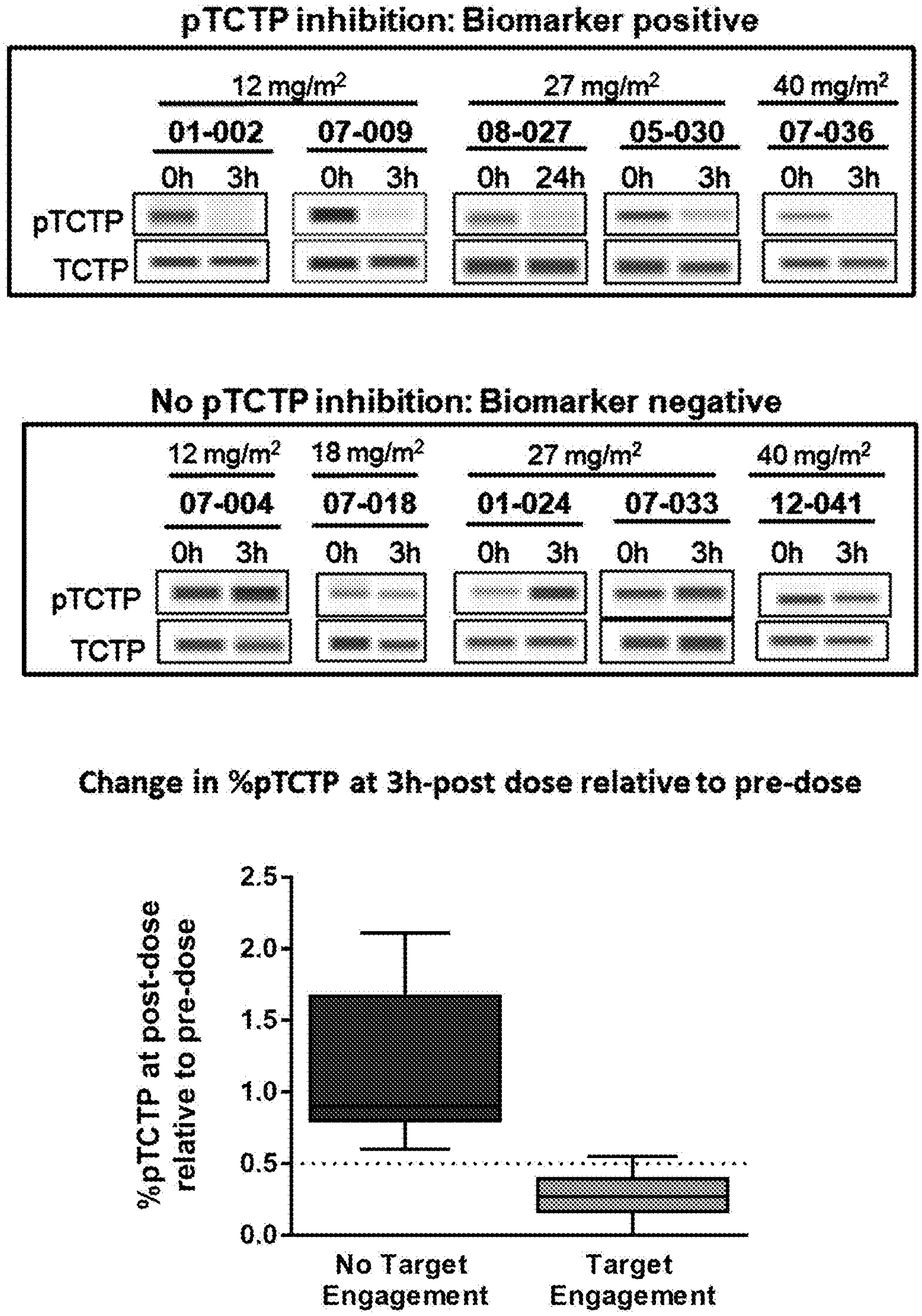
FIG. 8 shows western blots of PLK1 phosphorylation of TCTP before and after treatment of patients with one dose of onvansertib, and a graph showing the change in % pTCTP after treatment relative to before treatment.

Results are shown in FIG. 8. The top and middle panels show examples of western blots of samples from patients with biomarker positive, and biomarker negative pTCTP inhibition, respectively. Nine out of the 24 evaluable patients (38%) were biomarker positive. Biomarker positivity was not dependent on onvansertib dose, pharmacokinetics, nor single-agent effects of LDAC or decitabine.

Of the biomarker positive patients, 01-002 and 08-027 were being treated with LDAC; 07-009, 05-030, and 07-036 were being treated with decitabine. Of the biomarker negative patients, 07-018 and 07-033 were treated with LDAC; 07-004, 01-024 and 12-041 were treated with decitabine. This confirms that treatment with either LDAC or decitabine apparently does not affect the ability of a PLK1 inhibitor (here, onvansertib) to inhibit phosphorylation of a PLK1 target (here, TCTP).

Biomarker positive patients were being treated with onvansertib 12, 27 or 40 $mg/m^2$ and biomarker negative patients were being treated with onvansertib 12, 18, 27 and 40 $mg/m^2$. This indicates that biomarker positivity is not dependent on onvansertib dose. In addition, pharmacokinetics analysis showed no correlation between biomarker positivity and onvansertib concentration in blood.

The bottom panel of FIG. 8 shows the range of % pTCTP at post-dose relative to pre-dose for biomarker positive ("Target Engagement") and biomarker negative ("No Target Engagement") patients.

Figure 9A:
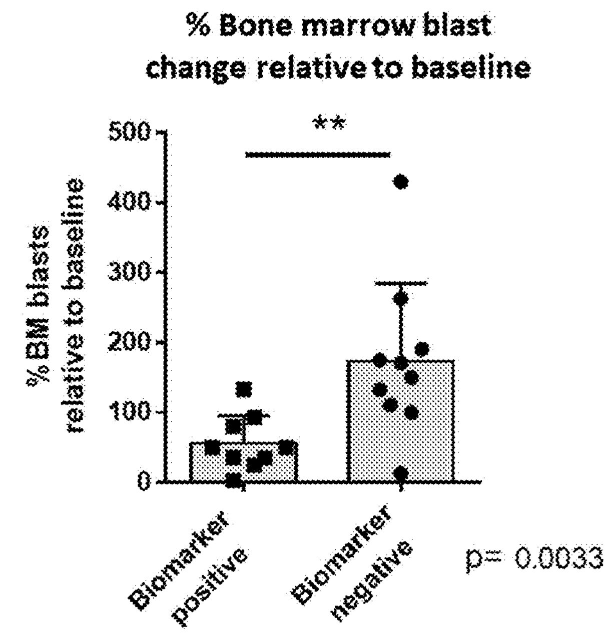
FIG. 9A is a graph showing % bone marrow blast change in patients whose TCTP phosphorylation is inhibited by onvansertib (biomarker positive), and patients whose TCTP phosphorylation is not inhibited by onvansertib (biomarker negative).
Figure 9B:
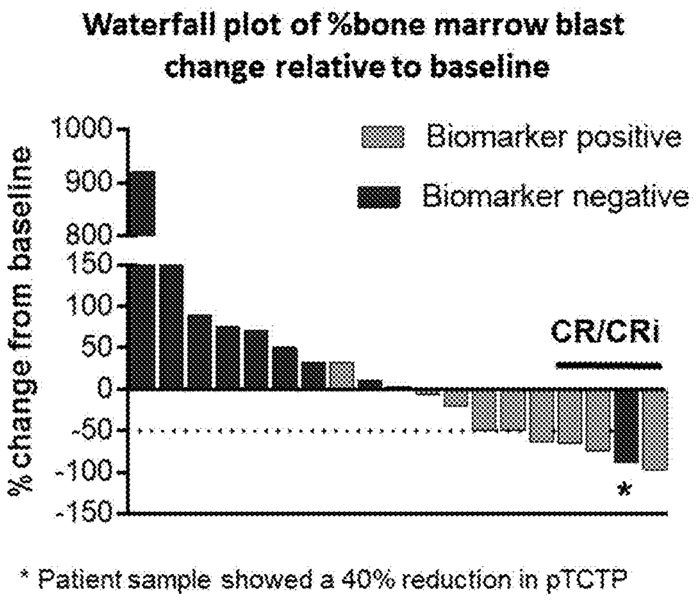
FIG. 9B is a waterfall blot of % bone marrow blast changes relative to baseline in biomarker positive patients and biomarker negative patients.

FIGS. 9A and 9B show that biomarker positivity predicts response to treatment. FIG. 9A shows that biomarker positive patients had a significantly greater decrease in BM blasts compared to biomarker negative patients. As shown in FIG. 9B, six out of the nine biomarker positive patients had a decrease in BM blasts≥50%. Four patients had a complete response [CR] or CR with incomplete hematological recovery [CRi], as defined in Cheson et al. (2003). Among the 4 patients with objective responses (CR+CRi), 3 were biomarker positive and 1 had a 40% decrease in pTCTP.

REFERENCES

Acunzo et al., 2014, Cancer Treatment Rev. 40:760-769.
Beria et al., 2011, Bioorg Med Chem Lett 21:2969-2974.
BioRad, 2017, ELISA—The Essentials, 20 pp.
Cancer Cell Line Encyclopedia (2012). Nature 483:603-607.
Cancer Genome Atlas, https://cancergenome.nih.gov/
Cancer Therapeutics Response Portal V2 (2013), Cell 154 (5): 1151-1161.
Casolaro et al., 2013, PLOS ONE 8: e58424.
Cheson et al., 2003, J. Clin. Oncol. 21:4642-4649.
Cucchi et al., 2010, Anticancer Res. 30:4973-4986.
Degenhardt et al., 2010, Clin Cancer Res 16:384-389.
Döhner et al., 2014, Blood 124:1426-1433.
Geeleher et al., 2017, Genome Research 27:1743-1751.
Genomics of Drug Sensitivity in Cancer (2013), Nucleic Acids Research 41 (D1): D955-D961.
Hartsink-Segers et al., 2013, Haematologica 98:1539-1546.
Liu et al., 2017, Translational Oncology 10:22-32.
Müller-Tidow et al., 2013, Br, J, Haematol. 163:214-222.
ClinicalTrials.gov, NCT03303339, PCM-075 in Combination With Either Low-dose Cytarabine (LDAC) or Decitabine in Adult Patients With Acute Myeloid Leukemia (AML).
Racila et al., 1998, Proc. Natl. Acad. Sci. USA 95:4589-4594.
Schöffski et al., 2012, Eur J Cancer 48:179-186.
Sero et al., 2014, Invest New Drugs 32:1167-1180.
The Cancer Genome Atlas-http://cancergenome.nih.gov/
UniProtKB P13693, Entry version 204 (31 Jul. 2019), at https://www.uniprot.org/uniprot/P13693.
Valsasina et al., 2012, MCT 1006-1016.
Weiss et al., 2017, Invest. New Drugs DOI 10.1007/s10637-017-0491-7.
U.S. Pat. No. 8,614,220.
U.S. Pat. No. 8,648,078.
U.S. Pat. No. 8,927,530.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method, comprising determining polo-like kinase 1 (PLK1) activity in a patient with a cancer by measuring phosphorylation of a PLK1 target of a cancer sample from the patient (a) prior to a treatment of the patient with a PLK1 inhibitor and (b) after the treatment of the patient with the PLK1 inhibitor, wherein the cancer is acute myeloid leukemia (AML), the PLK1 inhibitor comprises onvansertib, and the PLK1 target is translational control tumor protein (TCTP), wherein measuring phosphorylation of the TCTP of the cancer sample from the patient after the treatment of the patient with the PLK1 inhibitor comprises measuring phosphorylation of serine 46 of TCTP from about 3 hours to 5 days after the treatment of the patient with the PLK1 inhibitor;

selecting the patient for receiving further treatment with the PLK1 inhibitor if the phosphorylation of TCTP of the cancer sample from the patient (b) after the treatment is reduced at least 50% relative to the phosphorylation of TCTP of the cancer sample from the patient (a) prior to the treatment; and administering an effective amount of onvansertib to the selected patient, thereby treating AML in the selected patient, wherein the cancer sample is a blood sample.

2. The method of claim 1, wherein the PLK1 target is in cells of the cancer or is cell-free in blood of the patient.

3. The method of claim 1, wherein the patient is not selected for receiving further treatment with the PLK1 inhibitor unless the determined PLK1 activity from the patient (a) prior to the treatment of the patient with the PLK1 inhibitor when compared to non-cancerous cells is elevated.

4. The method of claim 1, wherein the patient is not selected for receiving further treatment with the PLK1 inhibitor if the determined PLK1 activity from the patient (a) prior to the treatment of the patient with the PLK1 inhibitor is below normal.

5. The method of claim 1, wherein the phosphorylation of the PLK1 target is measured immunochemically.

6. The method of claim 1, wherein a reduction of at least 50% in the phosphorylation of the PLK1 target after treatment with the PLK1 inhibitor indicates that the treatment is effective.

7. The method of claim 1, wherein the selected patient is also treated with cisplatin, cytarabine, decitabine, doxorubicin, gemcitabine, paclitaxel, SN38, sorafenib, velcade, abiraterone, ibrutinib, acalabrutinib, azacitidine, venetoclax, CPT11, 5FU, bevacizumab, bortezomib, a histone deacetylase inhibitor, or a combination thereof.

8. The method of claim 1, wherein the cancer sample is collected at about 3 hours after the treatment of the patient with the PLK1 inhibitor.

9. The method of claim 1, wherein the cancer has elevated PLK1 activity when compared to non-cancerous cells.

* * * * *